(12) United States Patent
Li

(10) Patent No.: US 9,038,202 B2
(45) Date of Patent: May 26, 2015

(54) MEANS TO SECURE A LENS INTO LENS FRAME OF A SNOW GOGGLE

(75) Inventor: Huei-Lung Li, Tainan (TW)

(73) Assignee: BORRION ENTERPRISE CO., LTD., Tainan (TW)

( * ) Notice: Subject to any disclaimer, the term of this patent is extended or adjusted under 35 U.S.C. 154(b) by 652 days.

(21) Appl. No.: 13/349,410

(22) Filed: Jan. 12, 2012

(65) Prior Publication Data

US 2013/0097855 A1   Apr. 25, 2013

(30) Foreign Application Priority Data

Oct. 20, 2011   (TW) ............................ 100219724 U

(51) Int. Cl.
  *A41B 11/02*   (2006.01)
  *A61F 9/02*    (2006.01)

(52) U.S. Cl.
  CPC . *A61F 9/025* (2013.01); *Y10T 29/53* (2015.01)

(58) Field of Classification Search
  CPC ............ A61F 9/025; A61F 9/02; G02C 9/04; G02C 9/00
  USPC ............ 2/426, 431–435, 438–439, 445–448, 2/454, 441; 351/44, 158
  See application file for complete search history.

(56) References Cited

U.S. PATENT DOCUMENTS

| | | | | |
|---|---|---|---|---|
| 5,182,586 | A * | 1/1993 | Bennato ........................... | 351/47 |
| 5,410,763 | A * | 5/1995 | Bolle ............................... | 2/436 |
| 5,867,841 | A * | 2/1999 | Chiang ............................. | 2/436 |
| 6,047,410 | A * | 4/2000 | Dondero .......................... | 2/426 |
| 6,735,788 | B2 * | 5/2004 | Chen-Lieh ........................ | 2/428 |
| 6,745,404 | B2 * | 6/2004 | Chen-Lieh ........................ | 2/428 |
| 7,080,415 | B2 * | 7/2006 | Wiedner .......................... | 2/435 |
| 7,126,732 | B2 * | 10/2006 | McNeal et al. .................... | 2/436 |
| 7,404,217 | B2 * | 7/2008 | Polinelli et al. .................. | 2/435 |
| 7,448,750 | B2 * | 11/2008 | Tackles ..................... | 351/159.01 |
| 7,743,432 | B2 * | 6/2010 | Curci .............................. | 2/435 |
| 8,192,015 | B2 * | 6/2012 | Taylor et al. .................... | 351/60 |
| 8,316,470 | B2 * | 11/2012 | McNeal et al. .................... | 2/438 |
| 2005/0210568 | A1 * | 9/2005 | Sheldon ........................... | 2/426 |
| 2006/0275101 | A1 * | 12/2006 | Feldman et al. ............... | 411/456 |
| 2008/0155736 | A1 * | 7/2008 | Paulson et al. .................. | 2/441 |
| 2008/0196149 | A1 * | 8/2008 | Takeshi et al. .................. | 2/425 |
| 2008/0301857 | A1 * | 12/2008 | Wang-Lee ........................ | 2/431 |
| 2010/0229291 | A1 * | 9/2010 | Tominaga et al. ............... | 2/431 |
| 2011/0219523 | A1 * | 9/2011 | Chiang ............................ | 2/434 |
| 2011/0258760 | A1 * | 10/2011 | Renaud-Goud et al. .......... | 2/431 |
| 2012/0255104 | A1 * | 10/2012 | Didier .............................. | 2/426 |
| 2012/0291186 | A1 * | 11/2012 | Cheng ............................. | 2/431 |
| 2013/0083285 | A1 * | 4/2013 | McNeal et al. ................ | 351/140 |

FOREIGN PATENT DOCUMENTS

| | | |
|---|---|---|
| TW | M358982 (U) | 6/2009 |
| TW | M395842 (U) | 1/2011 |

* cited by examiner

*Primary Examiner* — Shaun R Hurley
*Assistant Examiner* — Andrew W Sutton
(74) *Attorney, Agent, or Firm* — Muncy, Geissler, Olds & Lowe, P.C.

(57) ABSTRACT

This invention relates to a means of securing a lens member into a snow goggle frame member, wherein the goggle frame member includes first insertion apertures, with first locating blocks at front edge, the lens member has a lens secured thereon, the lens includes first troughs to receive a corresponding first block therein, a pair of first rails are formed at respective sides of the first trough, each first rail has a first notch which includes a pair of second notches thereat, retainers are secured to the goggle frame and lens frame respectively, one end of the first insertion aperture includes a first insertion post at one end and a first insertion section at the other end thereof to receive the first insertion post therein, the first insertion section is then inserted into the first notch. The goggle may be replaced with various lenses and secured firmly.

4 Claims, 7 Drawing Sheets

MEANS TO SECURE A LENS INTO LENS FRAME OF A SNOW GOGGLE

BACKGROUND OF THE INVENTION

1. Field of the Invention

This invention relates to means of securing a lens member into a snow goggle frame member, and more particular, to a means utilizing retainers to replace and to secure the lens to the goggle frame firmly.

2. Field of the Background

There are a number of related patents issued by the ROC (Republic of China), one of these patents No. M358982 disclosed a goggle frame member and a lens member, the goggle frame member has a restriction section formed along the edge corresponding to apertures of the lens, the restriction section has a channel with a block therein, the lens comprises a hook corresponding to the block of the channel, when the lens is inserted into the channel and hooked by the block of the channel and the lens is secured to the frame member firmly. A strap is fastened to the apertures at respective ends to secure the lens frame.

The lens of the patent, as described above has a portion blocked by the channel that narrows the wearer's vision.

Another patent issued also by the ROC with a patent No. M395842 has disclosed a goggle lens frame, a detachable lens and two retainers adapted to secure the lens to the frame. By disengaging the retainers, a pair of retainer blocks of the retainers will be released from the notches and the lens may be removed freely from the frame, and most important thing is there is no tool required to replace the lens.

However, the retainer of this patent requires a precise measurement in manufacture, or it may have problems to either holding or inserting the lens to the frame tightly.

SUMMARY OF THE INVENTION

In view of the shortcomings as described above, the present invention provides a means to secure a lens into a goggle lens frame which comprises a lens frame member having a lens receptacle with a plural first insertions thereon, each first insertion aperture has a first locating block at the front edge thereof, a lens member to be fitted in the lens receptacle of the lens frame member, comprises a plural first troughs for said locating blocks to sit therein, each first trough comprises a first rail extending from respective sides thereof and is connected to a first notch, each of the first notches is extending from respective ends thereof forming a second rail thereat, a plural retainers are adapted to hold the lens member to the lens frame member, one end of the first retainer comprises a first insertion post and a first insertion section slanted formed at the other end thereof, each insertion post is inserted into a corresponding first insertion aperture, and each insertion section is secured in a corresponding first notch. A strap is fastened to the lens receptacle of the lens frame member, and is comprised a pair of fixtures at respective ends.

The lens receptacle comprises a second insertion aperture at respective ends. Each second insertion aperture comprises a square-shaped second locating block at front edge thereof. A pair of second troughs is formed at respective side of the lens member corresponding to the apertures, each second trough is provided to secure a corresponding second locating block therein. A second notch is formed by extending from the second trough towards the edge of the lens member. A plural second retainers is adapted, each second retainer comprises a round-shaped second insertion post at one end and a slanted-shaped second insertion section at the other end thereof. Each second insertion post is inserted into a corresponding second insertion aperture. The front edge of the second insertion post has a second bulging block thereat. Each second insertion section is inserted into a corresponding second notch.

The lens frame member comprises a number of third insertion apertures on top and bottom ends thereof, and the fixture comprises a number of third insertion posts thereat. At the front end of each third insertion post there is a groove to receive a longitudinal block therein, the longitudinal block has a clamp trough to secure the strap ends therein Each of the above mentioned first locating block has a round pillar shaped and each first trough has a corresponding shape to the first locating block.

The first insertion post is in a round shape.

It is the primary object of the present invention to provide a means to secure a lens into a lens frame of a goggle which utilizes a first retainer and a second retainer to secure the lens to the lens frame that and to minimize contacting area to avoid fraction.

It is another object of the present invention to provide the means to secure a lens into a lens frame of a goggle which comprises a number of first retainers and a number of second retainers, each retainer has a compact size and has a light weight.

It is still another object of the present invention to provide the means to secure a lens into a lens frame of a goggle which enables the lens to be detached from the lens frame and replaced with another lens in an easy and rapid manner.

It is a further object of the present invention to provide the means to secure a lens into a lens frame of a goggle which utilizes retainers to secure the lens member to the lens frame member, and the connection minimizes blocking wearer's view.

DETAILED DESCRIPTION OF THE PREFERRED EMBODIMENT

Figure 1:
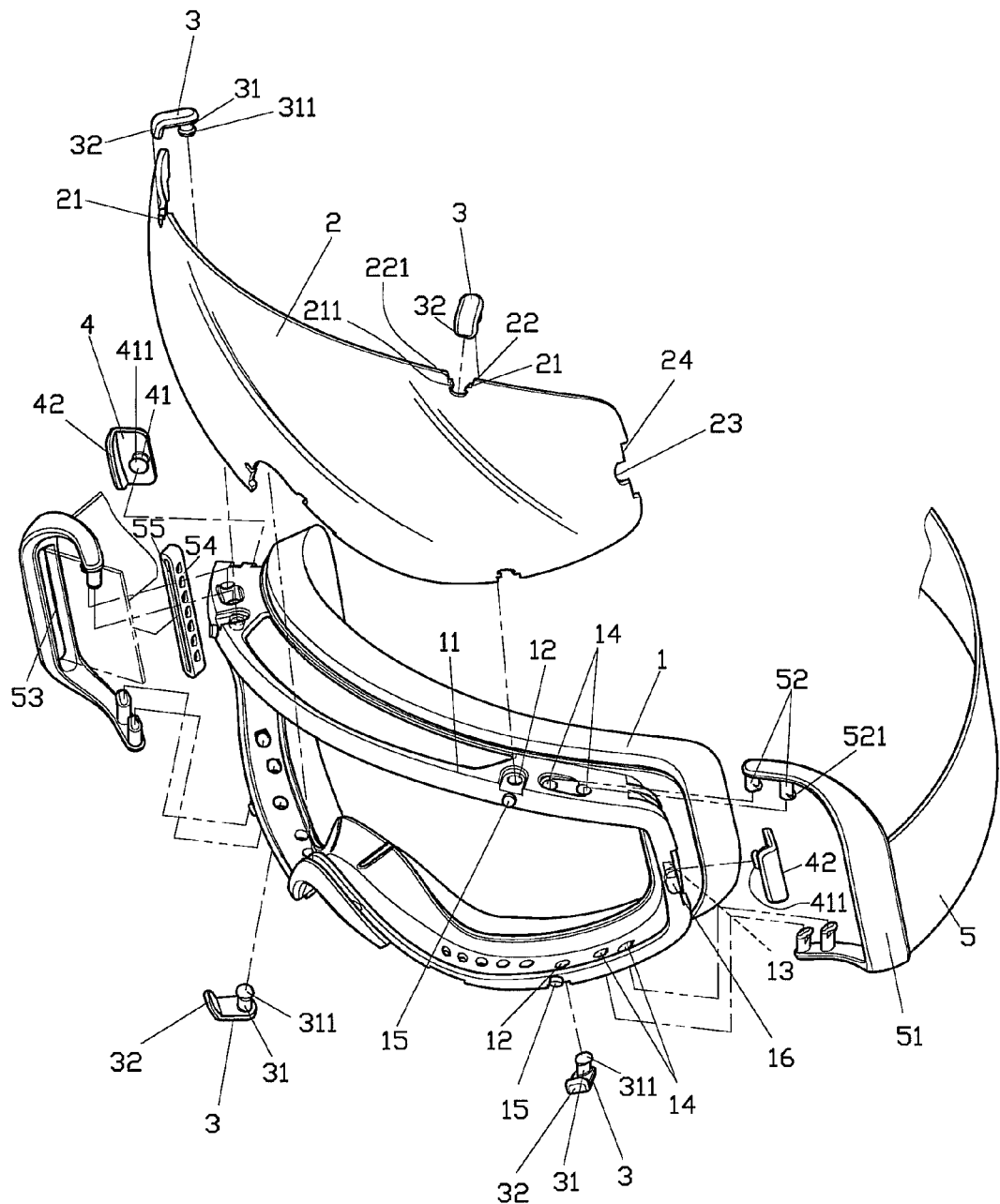
FIG. 1 is an exploded view of the present invention.

A means of securing a lens member into a goggle frame member of the present invention comprises a lens frame member 1, a lens 2, a number of first retainers 3, a number of second retainers 4, and a strap 5.

The frame member 1 comprises a lens receptacle 11 which comprises a number of first insertion apertures 12 on the top and the lower ends, a number of second insertion apertures 13 at two sides of the lens receptacle 11. The lens receptacle 11 further comprises a number of third insertion apertures 14 on the top and lower end. Each first insertion aperture 12 comprises a round pillar shaped first locating block 15 at a front end thereof, and each second insertion aperture 13 comprises a square shaped second locating block 16 at a front end thereof.

The lens member 2 is inserted in the lens receptacle 11 of the lens frame member 1 and secured therein. A number of first troughs 21 are formed on the top and the lower ends of the lens corresponding to the first insertion apertures 12, respectively. Each first trough 21 receives a first locating block 15 to sit therein. At each side of each first trough 21, there is a first rail 211 and a first notch 22 extending from the rail 211 outwardly towards the edge of the lens 2. Each second notch 22 extends a second rail 221 outwardly towards the edge of the lens member 2. Both first rail 211 and second rail 221 are formed in a slanted manner that will facilitate the installation and preventing from sliding away, and also to secure the first locating block 15 firmly. The lens member 2 further comprises a pair of second troughs 23 at two sides corresponding to the second insertion apertures 13 to receive a corresponding second locating block 16 therein. Each second trough 23 has a second notch 24 extending outwardly towards the edge of the lens member 2.

The first retainers 3 are used to secure the lens member 2 to the lens receptacle 12 of the lens frame member 1. Each first retainer 3 has a round-shaped first insertion post 31 at one end and a slanted-shaped first insertion section 32 at the other end. The first insertion post 31 has a first bulging block 3111 at the front edge, and is secured in the first insertion aperture 12, while the first insertion section 32 is secured to the first notch 22.

The second retainers 4 are also used to secure the lens member 2 to the lens receptacle 12 of the lens frame member 1. Each second retainer 4 has a round second insertion post 41 at one end, and a slanting second insertion post 42 at the other end. The second insertion post 41 is secured in the second insertion aperture 13, and comprises a second bulging block 411 at the front edge thereof. The second insertion section 42 is secured in the second notch 24.

Figure 7:
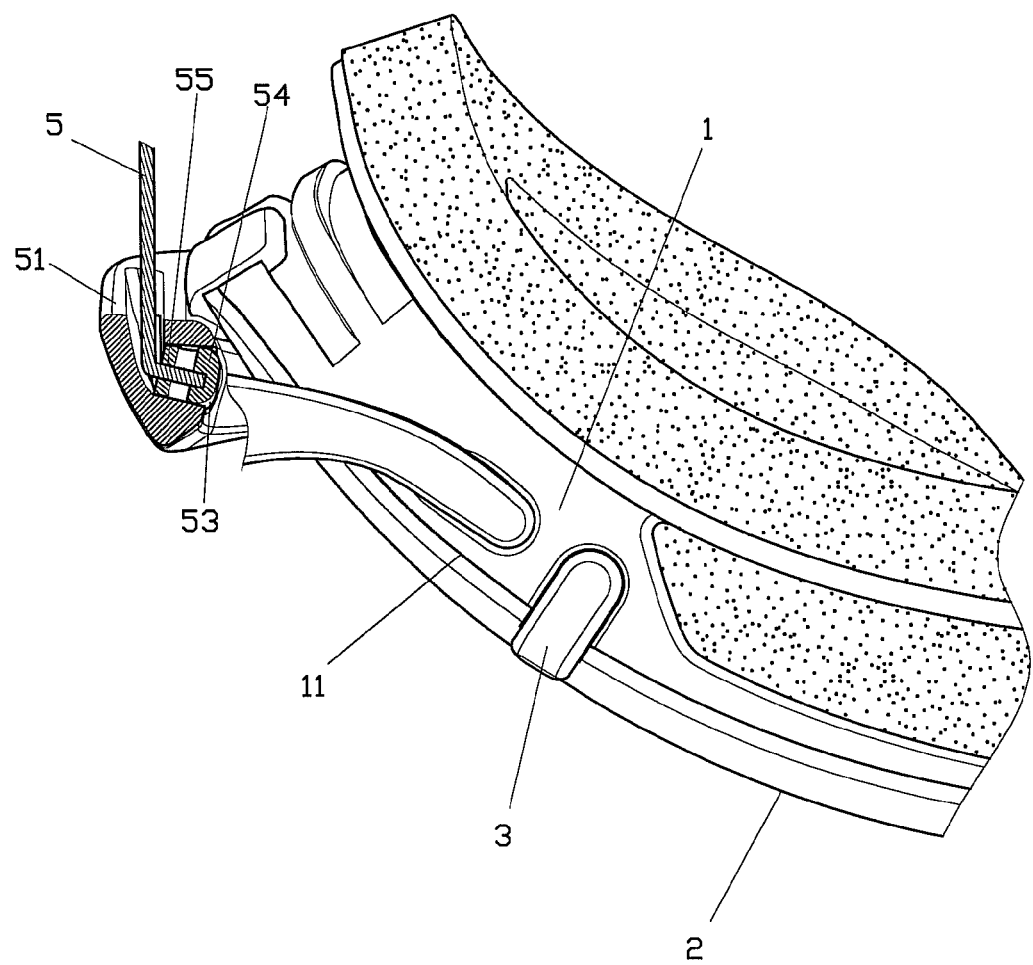
FIG. 7 is a partially cross sectional view showing a groove secured with a longitudinal block of the strap fixture

The strap 5 is fastened to the lens receptacle 11 of the lens frame member 1, and is composed of a pair of fixtures 51 at respective ends. Each fixture 51 has a third insertion post 52 to be secured in a corresponding third insertion aperture 14. A third bulging block 521 is formed at the front edge of the third insertion post 52. The fixture 51 comprises a groove 53 to receive a longitudinal block 54 therein. The longitudinal block 54 has a clamp trough 55 to secure the two ends of the strap 5 therein, as shown in FIG. 7. The longitudinal block 54 then is placed in the groove 53 so as to secure the strap 5 to the fixture 51.

Figure 2:
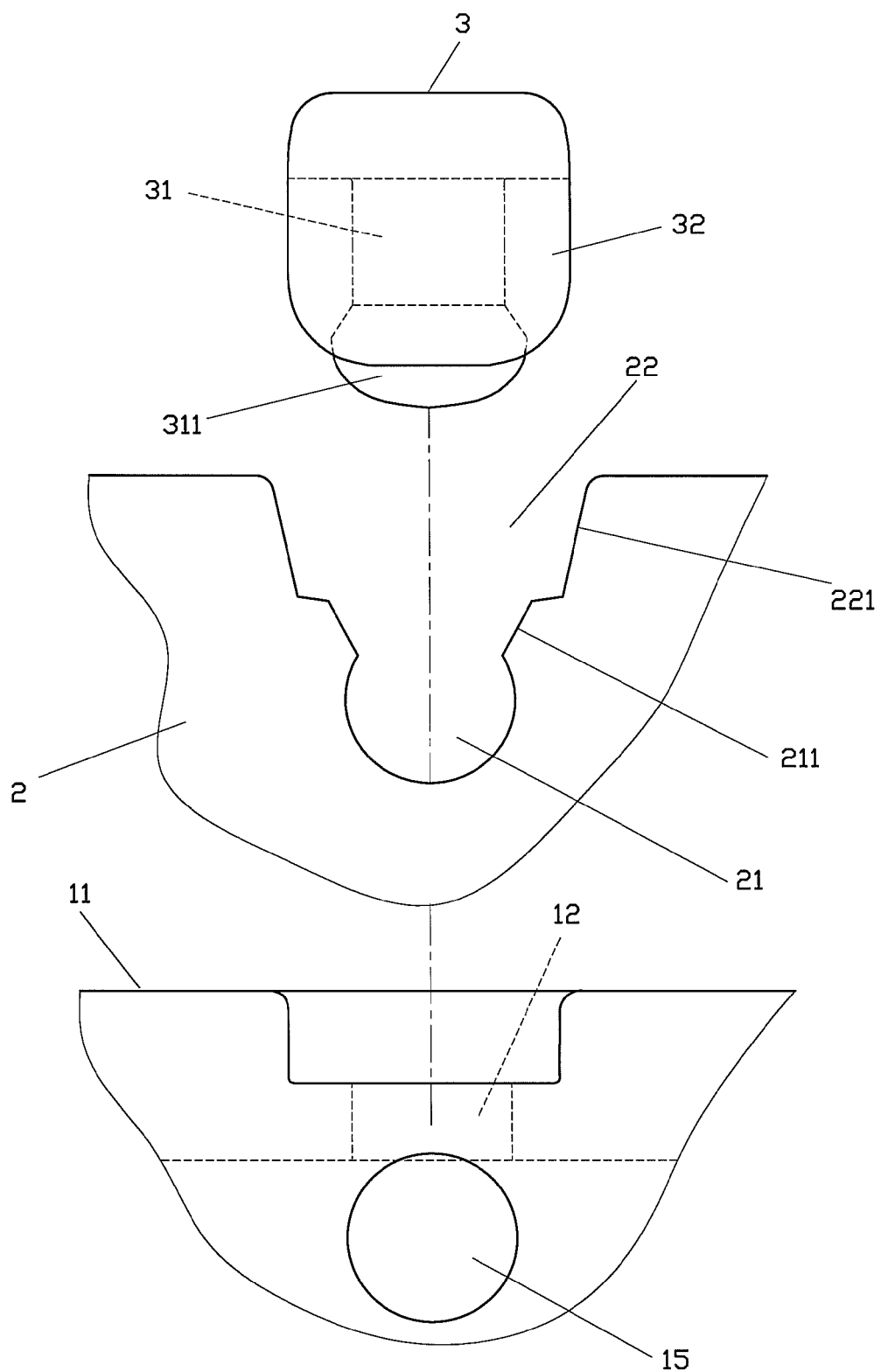
FIG. 2 is an enlarged view of a lens frame member, a lens member and a first retainer of the present invention.
Figure 3:
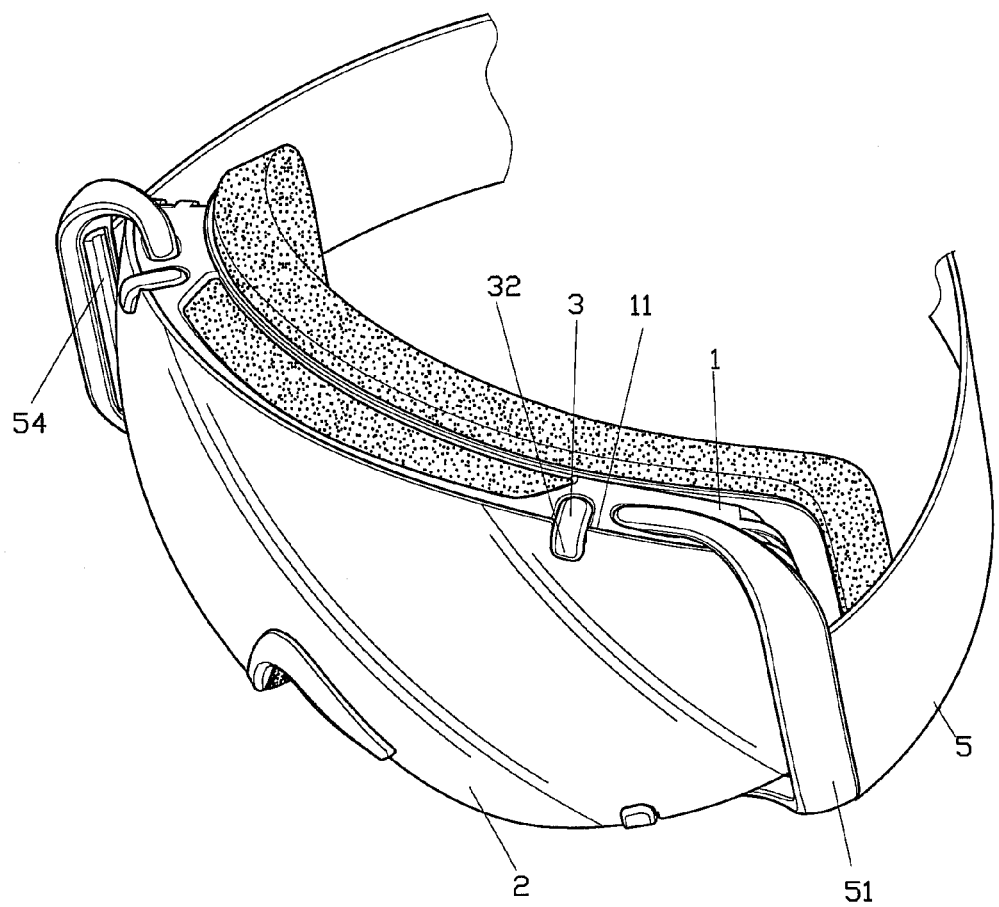
FIG. 3 is a perspective view of the assembled snow goggle of the present invention.
Figure 4:
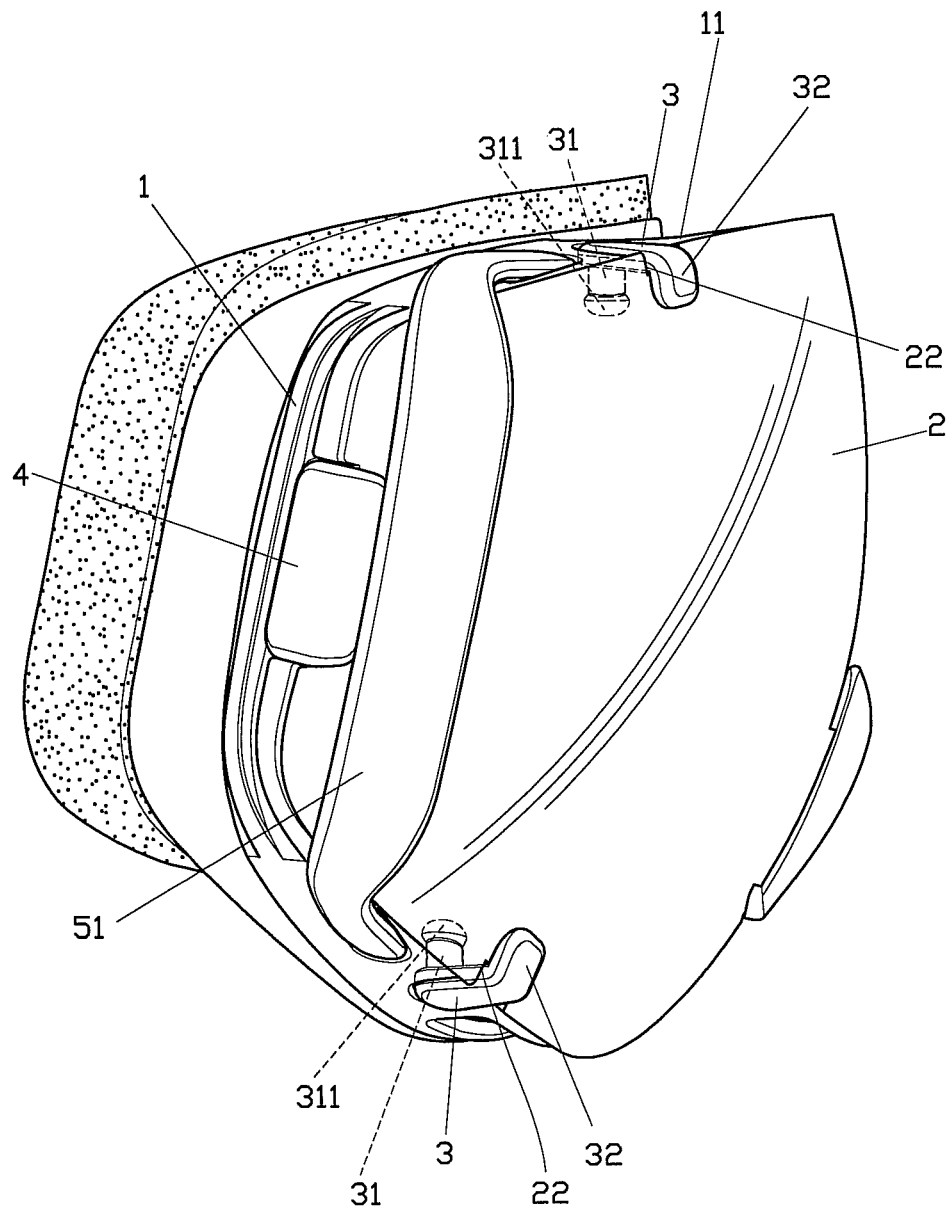
FIG. 4 is another perspective view showing a first retainer of the present invention secured a lens frame member.
Figure 5:
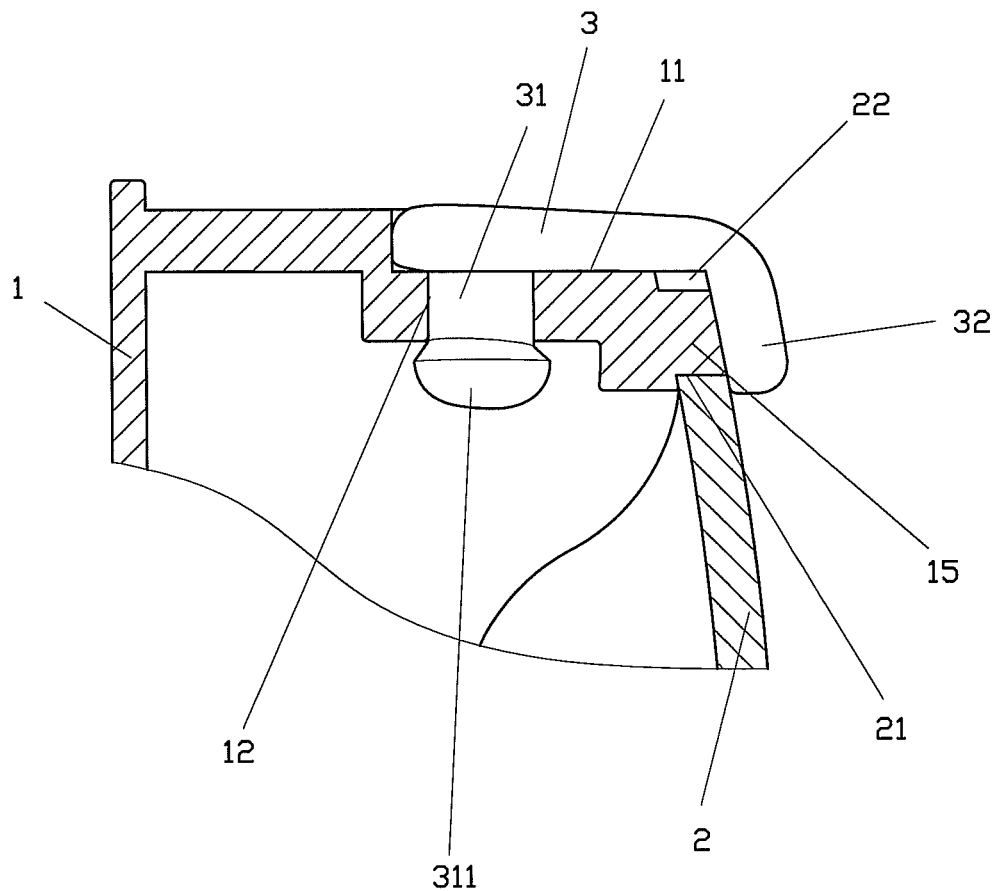
FIG. 5 is a cross sectional view showing the connection status between the first retainer and the lens frame member of the present invention.
Figure 6:
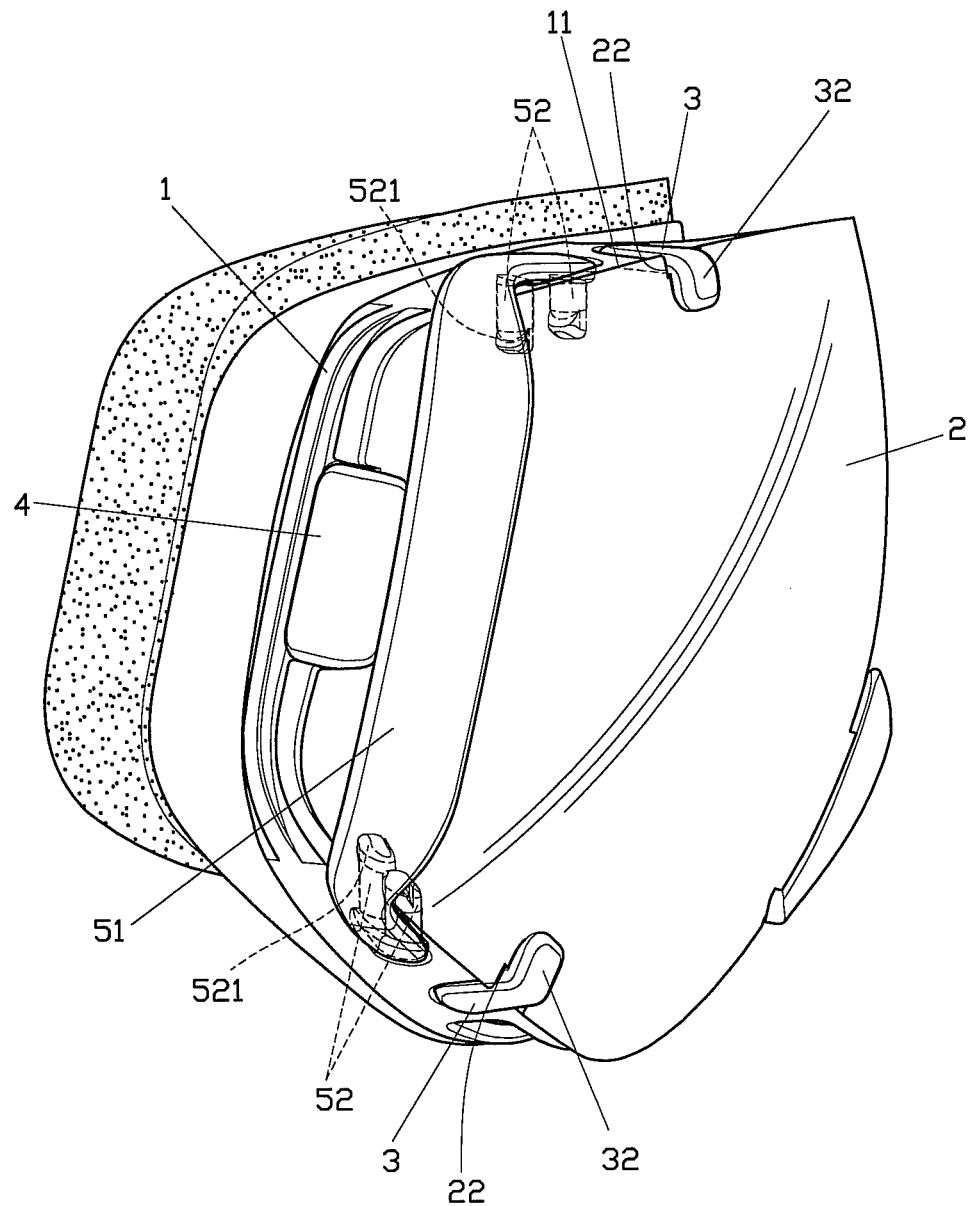
FIG. 6 is a perspective view of a strap fixture of the present invention securing the lens member.

To assemble the present invention, as shown in FIGS. 2 and 3, insert the lens member 2 into the lens receptacle 12 of the lens frame member 1, this will lead the first locating block 15 to slide through the second rail 211, the first rail 211 and to be secured in the first trough 21 of the lens member 2, as shown in FIGS. 4 and 5, and the lens member 2 will be secured thereat. The second locating block 16 at this time, will be secured in the second trough 23 of the lens member 2. The first insertion posts 31 of the retainers 3 are inserted into corresponding insertion apertures 12 of the lens receptacle 11 with the first bulging blocks 311 fitting in the first insertion apertures 12 to restrict the lens member 2 from moving up and down in the lens frame member 1. Whereas the first insertion sections 32 are secured in the first notches 22 of the lens member 2 and covers the first troughs 21 and the first locating blocks 15 to secure the lens member 2 from moving back and forth. The second insertion posts 41 of the retainers 4 are inserted into the second insertion apertures 13 of the lens receptacle 11 with their second bulging blocks 411 secured in the second insertion apertures 13, respectively, so that the second insertion apertures 42 may press and hold in the second notch 24 of the lens member 2, hence, the lens member 2 is secured in the lens receptacle 11 of the lens frame member 1. Now, secure the two ends of the strap 5 into the third insertion aperture 52 of the fixture 51, as shown in FIGS. 6 and 7, and the two fixtures 51 of the strap 5 in to the third insertion posts 14, whereas the third bulging blocks 521 are fastened in the third insertion apertures 14 securely, hence the strap 5 is secured to lens receptacle 11 of the lens frame member 1, and the goggle is ready to use. The tiny sizes of the first retainers 3 and the second retainers 4 will minimize blinding of user's view.

To replace the lens 2, referring to FIG. 1, detaches the first insertion posts 31 of the first retainers 3 from the first apertures 12, and the second insertion posts 41 of the first retainers 4 from the first apertures 13 to disengage the first insertion sections 32 from the first notches 22 of the lens member 2, as well as the second insertion sections 42 from the second notches 24 of the lens member 2, hence the lens member 2 may be detached from the lens receptacle 11 of the lens frame member 1, and a replacement lens 2 may be installed.

To replace the strap 5, as referring to FIGS. 1 and 6, pulls out the third posts 52 at two ends of the fixtures 51 from the third insertion apertures 14 of the lens receptacle 11 which enables the strap 5 to be detached from the lens receptacle 11 of the lens frame member 1.

While there has been described and illustrated one specific embodiment of the invention, it will be clear that variations in the details of the embodiment specifically illustrated and described may be made without departing from the true spirit and scope of the invention as defined in the appended claims.

I claim:

1. A device of securing a lens member into a snow goggle frame member, comprising:
    a lens frame member having a lens receptacle, said lens receptacle comprising a plurality of first insertion apertures and a plurality of first locating blocks, each of said first locating blocks is located adjacent to a front edge of a corresponding one of said first insertion apertures;
    a lens member secured to said lens receptacle and comprising a plurality of first troughs adapted to correspondingly receive said first locating blocks so that said lens member is restricted from moving left and right, each said first troughs has an arc-shaped rim from which a pair of first rails and a air of second rails sequentially extend outwardly towards an edge of said lens member to form a first notch corresponding to and communicating with said first troughs;
    a plurality of first retainers adapted to secure said lens member to said lens receptacle of said lens frame member, each of said first retainers has one end provided with a first insertion post and an other end provided with a first insertion slant, wherein each of said first insertion posts is inserted into a corresponding one of said first insertion apertures, while each of said first insertion slants is secured in a corresponding one of said first notches so that said lens member is restricted from moving back and forth; and
    a strap secured to said lens receptacle of said lens frame member, said strap comprising a pair of fixtures at respective ends,
    wherein said lens receptacle has two lateral edges each being provided with a second insertion aperture and a second locating block, each of said second locating blocks is located adjacent to a front edge of a corresponding one of said second insertion aperture, wherein said lens member has two lateral edges each being provided with a second trough and a second notch communicating with said second trough, each of said second trough is adapted to receive a corresponding one of said second locating blocks, and wherein a plurality of second retainers are further provided, each of said second retainers has one end provided with a cylindrical second insertion post and an other end provided with a second insertion slant, each of said second insertion posts is inserted into a corresponding one of said second insertion apertures, while each of said second insertion slants is secured in a corresponding one of said second notches.

2. The device of securing a lens member into a snow goggle frame member, as recited in claim 1, wherein said lens receptacle has an upper edge and a lower side each being provided with a third insertion aperture, and each said fixture comprises a third insertion post to be inserted into a corresponding said third insertion aperture, and wherein each said fixture comprises a groove to secure a longitudinal block therein, and each said longitudinal block comprises a clamp trough through which two ends of the strap is threaded.

3. The device of securing a lens member into a snow goggle frame member, as recited in claim 1, wherein said first locating blocks are formed as round protrusions to which said first troughs correspond in shape, so that each said first locating block is allowed to be received in a corresponding one of said first troughs.

4. The device of securing a lens member into a snow goggle frame member, as recited in claim 1, wherein said first insertion post has a cylindrical shape.

\* \* \* \* \*